(12) United States Patent  
Burges

(10) Patent No.: US 8,926,152 B2  
(45) Date of Patent: Jan. 6, 2015

(54) RING LIGHT ILLUMINATOR, BEAM SHAPER AND METHOD FOR ILLUMINATION

(75) Inventor: Dacian Burges, Dworp (BE)

(73) Assignee: KLA-Tencor Corporation, Milpitas, CA (US)

( * ) Notice: Subject to any disclaimer, the term of this patent is extended or adjusted under 35 U.S.C. 154(b) by 378 days.

(21) Appl. No.: 13/376,417

(22) PCT Filed: Jul. 25, 2011

(86) PCT No.: PCT/IB2011/053300  
§ 371 (c)(1),  
(2), (4) Date: Dec. 6, 2011

(87) PCT Pub. No.: WO2012/014141  
PCT Pub. Date: Feb. 2, 2012

(65) Prior Publication Data  
US 2012/0188786 A1    Jul. 26, 2012

Related U.S. Application Data

(60) Provisional application No. 61/369,632, filed on Jul. 30, 2010.

(51) Int. Cl.

| | | |
|---|---|---|
| F21V 7/04 | (2006.01) | |
| G02B 21/08 | (2006.01) | |
| G01N 21/88 | (2006.01) | |
| F21V 8/00 | (2006.01) | |
| G02B 19/00 | (2006.01) | |
| G02B 27/09 | (2006.01) | |

(52) U.S. Cl.  
CPC .......... *G02B 21/084* (2013.01); *G01N 21/8806* (2013.01); *G02B 6/0006* (2013.01); *G02B 6/0008* (2013.01); *G02B 19/0061* (2013.01); *G02B 27/0994* (2013.01); *G01N 2021/8822* (2013.01); *G01N 2201/062* (2013.01); *G01N 2201/0631* (2013.01); *G01N 2201/0638* (2013.01)  
USPC .......................................... 362/551; 362/558

(58) Field of Classification Search  
USPC .......... 362/551, 555, 558, 582, 236, 244, 317  
See application file for complete search history.

(56) References Cited

U.S. PATENT DOCUMENTS

| | | | |
|---|---|---|---|
| 7,319,285 B2* | 1/2008 | Hanano | 313/111 |
| 2003/0072156 A1* | 4/2003 | Pohlert et al. | 362/244 |
| 2003/0231511 A1 | 12/2003 | Thibault | |
| 2004/0252376 A1 | 12/2004 | Gollier et al. | |
| 2006/0193641 A1* | 8/2006 | Callahan | 399/6 |
| 2009/0141503 A1 | 6/2009 | Phillips, III | |
| 2011/0122619 A1* | 5/2011 | Wilcox | 362/245 |

* cited by examiner

*Primary Examiner* — John A Ward  
(74) *Attorney, Agent, or Firm* — Suiter Swantz pc llo

(57) ABSTRACT

A ring light illuminator with annularly arranged light sources is disclosed. To each light source there corresponds a light collector, a homogenizing means for light from the light source, and an anamorphic system for imaging an output of the homogenizing means into an area to be illuminated. The anamorphic system compensates deformations of a cross-sectional area of a light beam in a surface to be illuminated due to an oblique angle of incidence of the light beam onto the surface. The homogenizing means in embodiments is a rod, into which light from the light collector is directed. The end of the rod opposite the light collector is imaged by the anamorphic system into the area to be illuminated on the surface. Also disclosed is a method for illumination.

29 Claims, 12 Drawing Sheets

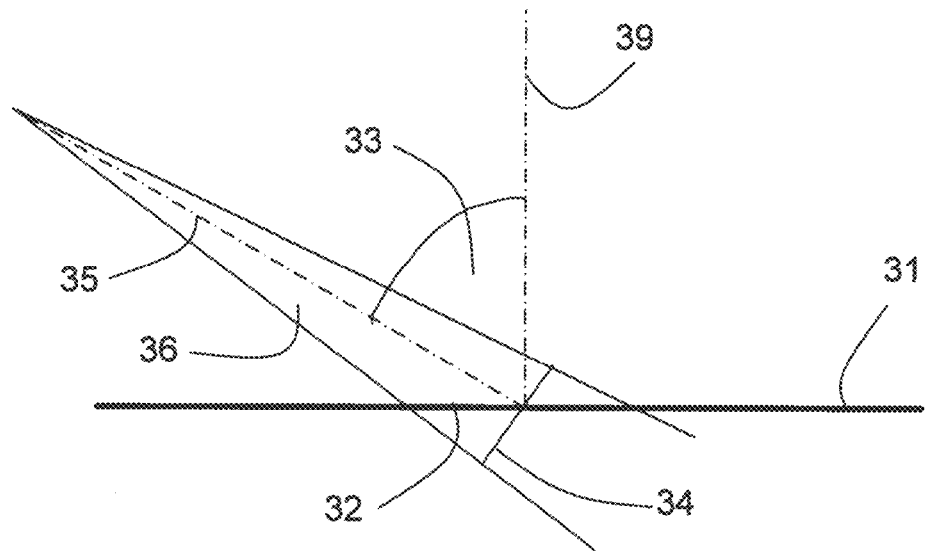
Fig. 6a
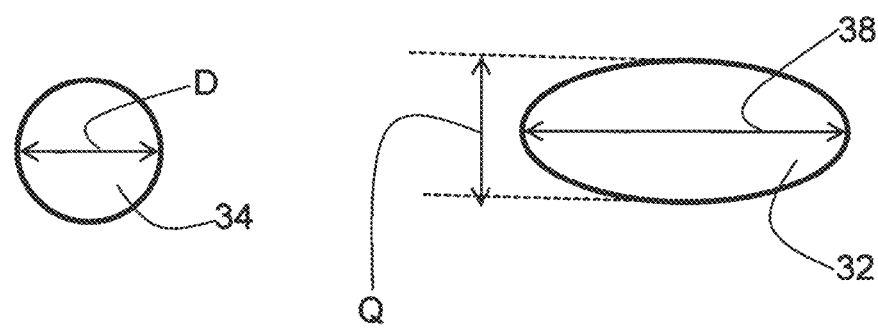
Fig. 6b
Fig. 6c

RING LIGHT ILLUMINATOR, BEAM SHAPER AND METHOD FOR ILLUMINATION

CROSS REFERENCE TO RELATED APPLICATIONS

This patent application claims priority of U.S. provisional patent application No. 61/369,632 filed Jul. 30, 2010, the application is incorporated herein by reference.

FIELD OF THE INVENTION

The present invention relates to a ring light illuminator.
The present invention also relates to a beam shaper.
The present invention also relates to a method for illumination.

BACKGROUND OF THE INVENTION

In many optical inspection or imaging tasks a well-defined illumination of the area to be inspected or imaged is required. For many such illumination purposes ring lights are used, for example in microscopy, where they are a common means to provide a dark field illumination. In such applications, it is desirable to restrict the area illuminated to the area of interest, and to have a homogeneous distribution of light within the area of interest. Possible light sources for example are arc lamps, LEDs (light emitting diodes), laser diodes, and halogen bulbs. While arc lamps typically provide higher light intensities than LEDs, they also exhibit stronger intensity fluctuations and shorter life times than LEDs; thus generally LEDs are a preferred choice of light source. As light from typical LEDs is emitted into a hemisphere around the LED, optical elements are required to direct as much as possible of the emitted light from one or plural LEDs into the area of interest, i.e. into the area to be illuminated.

The European Patent Application EP 1 919 001 A1 relates to a spot light device for product inspection, wherein an LED is used as light source. In order to homogenize the distribution of light across a certain area, the light from the LED is passed through a rod lens. The light from the LED is introduced into the rod lens by a condensing lens. In order to assure proper alignment of rod lens and condensing lens, and also in order to reduce the number of individual parts to be handled during assembly of an optical system, the rod lens and condensing lens are provided as sections of an optical unit, the rod lens constituting a light transmitting section and the condensing lens a light condensing section. The condensing section combines refraction and reflection in order to direct light from the light source into the transmitting section.

The European Patent Application EP 2 177 816 A2 discloses an array of light sources, in particular LEDs, the light of which is directed into a light integrator shaped as a rod. The light integrator homogenizes and constrains the light, based on reflection of the light within the integrator. The light integrator may be a hollow tube with reflective inner surface or a solid rod of an optically transparent material, where the reflection of light within the light integrator is due to total internal reflection. The cross-section of the light integrator may be circular, polygonal, or irregular. Further optical elements may be provided downstream from the light integrator. To each of the light sources there may correspond an optical element for controlling and directing the light from the light source. The light integrator may be tapered, in order to influence the divergence of the light exiting from the light integrator.

The European Patent Application EP 1 150 154 A1 discloses an illumination system, in particular for microscopes, wherein plural light sources, preferentially LEDs, are arranged in an annular carrier. The LEDs may be controlled individually or in groups, and exhibit a small angle of emission.

The German Patent Application DE 28 52 203 discloses an illumination setup for a microscope, where light from a light source is guided along optical fibres and exits the fibres at a respective end of the fibres, wherein these respective ends are arranged in an annular fashion. A further ring illumination system, based on optical fibres is for example disclosed in the German patent application DE 40 16 264.

A problem of ring illumination systems based on optical fibres is the large divergence of the light exiting an optical fibre. Likewise, annular arrangements of LEDs tend to create rather inhomogeneous illumination fields, and even if such LEDs are used in combination with state of the art collector lenses, the degree of homogeneity of the illumination field required for some applications is not achievable.

Maximum light intensity is a very important design parameter for ring lights, as these inherently are "dark field" illumination, where scattered light is often a viewing object. A main disadvantage of LEDs compared to arc lamps (a standard for bright illumination for normal microscope viewing), is that they are typically dimmer. It is often the case that LED based systems do not provide adequate light intensity at the viewed object, and that extreme care in design should be made to maximize the possible light at the image. Maximizing the light is particularly important in machine vision/inspection where integration time cannot be arbitrarily lengthened to increase the light energy available to create a well exposed image. Increase of the integration time in a machine vision system decreases the frequency of images and increases the total inspection time (image time). Since the value of an inspection machine depends on how many fields can be imaged in a fixed time, maximizing the light at the object is a very important feature.

With ring lights the area to be illuminated is typically illuminated under an oblique angle. The light beams from the individual light sources in the ring light impinge onto the surface to be illuminated in such a way that an angle between a surface normal and a central axis of a respective light beam is neither zero nor 90°. The cross section of a respective beam on the surface to be illuminated is larger than a cross section of the respective beam in the case of illumination of the surface along the surface normal. Therefore for the light beams in a ring light the intensity of the beams is distributed over a larger area on the surface than for illumination along the surface normal. The intensity of the light beams available on the surface thus is effectively reduced. In view of the above goal of maximum light intensity this is a disadvantage.

SUMMARY OF THE INVENTION

It is an object of the present invention to provide a ring light illuminator capable of creating a well-defined and homogeneous illumination field in an area to be illuminated on a surface. Additionally, light from a light source of the ring illuminator should be collected efficiently and directed to the area to be illuminated, despite an oblique angle of the illumination.

This object is achieved by a ring light illuminator for illuminating an area on a surface, comprising a plurality of annularly arranged light sources;

a light collector assigned to each light source and encompassing a light emitting surface of the respective light source; and an anamorphic system arranged in an optical axis of each light collector, configured to direct light into the area to be illuminated.

It is a further object of the invention to provide a beam shaper which collects light from a light source efficiently and allows to direct it onto a surface to be illuminated under an oblique angle without incurring a reduction of available light intensity at the surface due to the oblique angle of incidence. The illumination field created on the surface to be illuminated should also exhibit a high degree of homogeneity.

This object is achieved by a beam shaper comprising:

a light collector configured to encompass a light emitting surface of a light source;

a homogenizing rod configured to homogenize light received from a light collector; and an anamorphic system for imaging an end of the homogenizing rod opposite the light collector into an area to be illuminated.

It is yet another object of the invention to provide a beam shaper which collects light from a light source efficiently and allows to direct it onto a surface to be illuminated under an oblique angle without incurring a reduction of available light intensity at the surface due to the oblique angle of incidence. The beam shaper moreover shall be of a compact design.

This object is achieved by a beam shaper comprising:

a light collector configured to encompass a light emitting surface of a light source; and an anamorphic optical system arranged on an optical axis of the light collector configured to receive light from the light source and to direct it onto an area to be illuminated.

The ring light illuminator according to the invention comprises a plurality of light sources arranged in an annular fashion. In preferred embodiments each light source is a light emitting diode (LED) or an array of LEDs. According to the invention a light collector is assigned to each light source. The light collector is configured in such a way that it encompasses a light emitting surface of the respective light source. Due to this arrangement light emitted from the light emitting surface of the light source reaches the light collector and is collected by it. Furthermore according to the invention in an optical axis of the light collector an anamorphic system is provided. Light collected by the light collector reaches the anamorphic system, which directs the light as a beam into the area to be illuminated on a surface. The light beam impinges on this surface under an oblique angle. The anamorphic system shapes the beam in such a way that the resulting cross section of the beam on the surface is within the area to be illuminated on the surface.

In addition to the anamorphic shaping of the beam by the anamorphic system, the anamorphic system in embodiments may perform an additional light focusing or lensing function. In specific embodiments this may be achieved by an anamorphic system which is a toroidal lens or a cylinder lens shaped in such a way that in addition to a purely anamorphic function an additional focusing of a light beam passing the toroidal lens or cylinder lens, respectively, is achieved. In different embodiments the anamorphic system has a first optical element with a light focusing function and a second optical element performing anamorphic beam shaping. In specific embodiments the second optical element may be a toroidal lens or cylinder lens, respectively, shaped in such a way that a light beam passing the second optical element does not experience additional focusing. It is obvious to a person skilled in the art that the anamorphic system can comprise plural optical elements. For example, instead of a single toroidal lens or cylinder lens, the anamorphic system may comprise an assembly of plural lenses, which together perform anamorphic beam shaping and optionally additional focusing of a light beam.

Anamorphic beam shaping generally refers to a deformation of a cross section of a beam in such a way that a diameter or width of the cross section of the beam in a first direction perpendicular to an optical axis of the beam is reduced or enlarged, while the width or diameter of the beam in a second direction perpendicular to the optical axis of the beam remains unmodified. With regard to ring light illuminators, in particular a reduction of the width or diameter of the beam in the first direction is relevant. Due to the oblique angle of incidence of a beam of light on a surface, as is the case with ring light illuminators, the diameter of the cross section of the beam on the surface along a direction in the surface defined by the intersection of the surface with the plane comprising the optical axis of the beam and the surface normal is enlarged. The anamorphic system is aligned in such a way that a reduction of the diameter or width of the beam in the first direction perpendicular to the optical axis of the beam fully or at least partially compensates the enlargement of the diameter of the cross section of the beam on the surface. The cross section of the beam on the surface depends also on the divergence of the beam, and preferentially the divergence of the beam is taken into account in the configuration of the anamorphic system, so that the required compensation of the enlargement of the diameter of the cross section of the beam on the surface can be achieved. In the case of a parallel beam, i.e. a beam with parallel light rays, showing neither convergence nor divergence, the diameter of the beam along the first direction perpendicular to the optical axis has to be reduced to the desired diameter on the surface times the cosine of the angle between the optical axis of the beam and the surface normal.

In advantageous embodiments there corresponds a homogenizing means to each light collector. The purpose of the homogenizing means is to reduce inhomogeneities of light intensity across the light beam, so that eventually the intensity of light across the diameter of a respective light beam is homogeneous to a sufficiently high degree. The precise meaning of sufficient in this context is defined by the specific requirements of the respective illumination task the ring light illuminator is used for.

In one preferred embodiment the homogenizing means is a rod of circular, elliptical, rectangular, square, hexagonal, octagonal or other cross-section; the cross-section herein is perpendicular to an axis of the rod which is aligned with an optical axis of the light collector. The rod has a first end, through which light is received from the light collector, and a second end, opposite the first end along the optical axis, through which the light exits the rod. From the second end of the rod the light reaches the anamorphic system and by that it is directed into the area to be illuminated. The homogenizing function of the rod is due to reflection, typically multiple reflection, of light from the sides of the rod parallel to the optical axis. Preferentially, the rod is a solid piece of matter, transparent at least for the wavelengths of light to be used for illumination, and the reflection is total internal reflection. Alternatively, the sides of the rod can be provided with a reflective coating, or the rod can be a hollow tube with reflective inner walls.

Advantageously, the rod and the light collector form an integral unit, and in particular may be manufactured as one piece. This reduces the number of individual parts which need to be handled in assembly or maintenance of the ring light illuminator, and also obviates the need to properly align the light collector and the rod during assembly or maintenance. Even more advantageously, light collector, rod, and anamorphic system form an integral unit and may be manufactured as one piece.

In alternative embodiments, the homogenizing means is a texture provided on the light collector.

As the operation of the light sources generates heat, advantageously a cooling mechanism for the ring light illuminator is provided. In embodiments, this cooling mechanism comprises cooling fins provided on the outer surface of the ring light illuminator, so that the surface for heat exchange with the environment of the ring light illuminator is increased. An alternative or additional cooling method is cooling with a liquid.

In a specific embodiment a ring light illuminator according to the invention for illuminating an area on a surface comprises a plurality of annularly arranged light sources. To each light source there is assigned a beam shaper, which is injection molded as one piece from a plastic material. The beam shaper therein exhibits a light collector portion encompassing a light emitting surface of one light source, wherein the function of the light collector portion is based on total internal reflection and on refraction. The beam shaper also exhibits a light homogenizing portion shaped as a rod, arranged and configured to receive light from the light collector portion through a first end of the rod. The light homogenizing function of the rod is based on total internal reflection of the light within the rod. The light exits the rod through a second end of the rod and reaches an anamorphic portion of the beam shaper. The anamorphic portion performs a lensing function (or light focusing function) and an anamorphic beam shaping function, by which it images the second end of the rod into the area to be illuminated on the surface. The image of the second end of the rod is anamorphically deformed in such a way that distortions of the image due to the oblique angle of incidence of the light onto the surface are fully or partially compensated.

Injection molding the beam shaper greatly simplifies manufacture. Manufacturing the beam shaper as one piece facilitates handling of the beam shaper, as no separate parts need to be assembled when the beam shaper is deployed in a ring light illuminator.

One possibility of the molding material for the beam shaper is acrylic, another one would be polycarbonate. Acrylic has better transmission than polycarbonate but is less capable of withstanding elevated temperatures. Acrylic should be ok for applications where the illumination source does not produce a lot of excess heat. The transmission losses in acrylic are roughly 0.25% per mm which results in a 15% loss in case the beam shaper has an overall length of 67 mm.

Beam shapers as described above are not limited to ring light illuminators.

A beam shaper according to the invention comprises a light collector configured to encompass a light emitting surface of a light source, a homogenizing rod configured to homogenize light received from a light collector, and an anamorphic system for imaging an end of the homogenizing rod opposite the light collector into an area to be illuminated.

The rod may be of circular, elliptical, rectangular, square, hexagonal, octagonal or other cross-section; the cross-section herein is perpendicular to an axis of the rod which is aligned with an optical axis of the light collector. The rod has a first end, configured to receive light collected by the light collector, and a second end, opposite the first end along the optical axis, through which light received through the first end exits the rod. From the second end of the rod the light reaches the anamorphic system and by it is directed into the area to be illuminated. The homogenizing function of the rod is due to reflection, typically multiple reflection, of light from the sides of the rod parallel to the optical axis. Preferentially, the rod is a solid piece of matter, transparent at least for the wavelengths of light to be used for illumination, and the reflection is total infernal reflection. Alternatively, the sides of the rod can be provided with a reflective coating, or the rod can be a hollow tube with reflective inner walls.

In embodiments the beam shaper may be made of a plastic material or glass, in particular the beam shaper may be manufactured as one piece, for example by injection molding. Acrylic or polycarbonate again are possible choices of molding materials.

In embodiments of the beam shaper the anamorphic system performs a light focusing function in addition to the anamorphic beam shaping function. In specific embodiments this may achieved by an anamorphic system which is a toroidal lens or a cylinder lens shaped in such a way that in addition to a purely anamorphic function an additional focusing of a light beam passing the toroidal lens or cylinder lens, respectively, is achieved. In different embodiments the anamorphic system has a first optical element with a light focusing function and a second optical element performing anamorphic beam shaping. In specific embodiments the second optical element may be a toroidal lens or cylinder lens, respectively, shaped in such a way that a light beam passing the second optical element does not experience additional focusing.

In a specific embodiment the beam shaper is injection molded as one piece from a plastic material and comprises a light collector portion, a light homogenizing portion, and an anamorphic portion. The light collector portion is configured to encompasses a light emitting surface of a light source. The function of the light collector portion is based on total internal reflection and on refraction. The light homogenizing portion is shaped as a rod. The rod is arranged and configured to receive light from the light collector portion through a first end of the rod. The light homogenizing function of the rod is based on total internal reflection of the light within the rod. The anamorphic portion is configured to image a second end of the rod opposite the first end of the rod into the area to be illuminated, therein performing a lensing function and an anamorphic beam shaping function.

Another beam shaper according to the invention comprises a light collector and an anamorphic system. The light collector is configured to encompass a light emitting surface of a light source. The anamorphic system is arranged on an optical axis of the light collector and configured to receive light from the light collector and to direct it onto an area to be illuminated. This beam shaper may be manufactured as one piece.

In an embodiment the anamorphic system exhibits a light focusing function.

Preferentially the light collector performs its light collecting function by a combination of total internal reflection and refraction.

In a specific embodiment the beam shaper is injection molded as one piece from a plastic material, and comprises a light collector portion and an anamorphic portion. The light collector portion is configured to encompass a light emitting surface of a light source. The light collecting function of the light collector portion in this embodiment is based on total internal reflection and on refraction. The anamorphic portion is configured to direct light from the light collector into the area to be illuminated, therein performing a lensing function and an anamorphic beam shaping function.

In the method according to the invention for homogeneously illuminating an area on a surface a plurality of light sources are arranged in an annular fashion about the area to be illuminated and at a distance from the surface. Light emitted by each light source is collected with a beam shaper into a respective beam of a predefined cross section. Herein an optical axis of the beam shaper is directed towards the surface under an oblique angle with the surface. The beam is to be directed into the area to be illuminated along the optical axis of the beam shaper and thus under an oblique angle with the surface. Such an oblique angle of incidence causes deformations of the cross-sectional area of the beam on the surface with respect to the cross section of the beam. Therefore, before each beam is directed into the area to be illuminated, its cross section is anamorphically deformed in such away that the deformation of its cross-sectional area on the surface is compensated, or, put differently, that the deformation of the cross-sectional area of the beam on the surface due to the oblique angle of incidence cancels the anamorphic deformation of the cross section of the beam.

BRIEF DESCRIPTION OF THE DRAWINGS

The nature and mode of operation of the present invention will now be more fully described in the following detailed description of the invention taken with the accompanying drawing figures, in which

FIG. 6a illustrates the general geometrical situation in the case of illumination of a surface by a light cone under an oblique angle.

FIG. 6b shows a cross section of a light cone of FIG. 6a, wherein the cross section is perpendicular to an optical axis of the light cone.

FIG. 6c shows a cross-sectional area of the light cone on the surface of FIG. 6a.

FIG. 10b is another perspective view of the light collector and the homogenizing rod of FIG. 10a;

DETAILED DESCRIPTION OF THE INVENTION

Figure 1A:
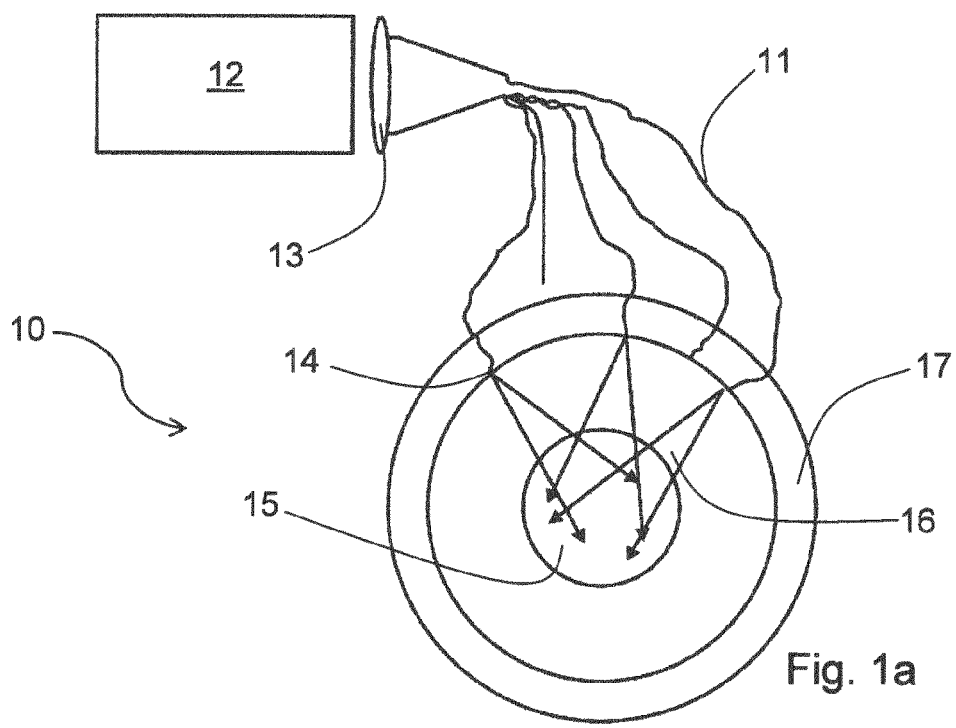
FIG. 1a shows a prior art ring light illuminator with annularly arranged ends of optical fibres.

Same reference numerals refer to same elements throughout the various figures. Furthermore, only reference numerals necessary for the description of the respective figure are shown in the figures. The shown embodiments represent only examples of how the invention can be carried out. This should not be regarded as limiting the invention.

FIG. 1a shows a setup for a prior art ring light illuminator 10. An arc lamp 12 is used as a light source; light from the arc lamp 12 is coupled into plural optical fibres 11 by suitable optical elements 13 (only one such element is shown in the drawing). Ends 14 of the optical fibres 11 are arranged annularly in a ring shaped carrier 17 of the ring light illuminator 10, in such a way that they emit the light from the arc lamp 12 towards an area 15 to be illuminated circumscribed by the carrier 17. As is indicated by the cones 16, the light is emitted from the ends 14 with a considerable divergence, meaning a divergence too large for many precision applications.

Figure 1B:
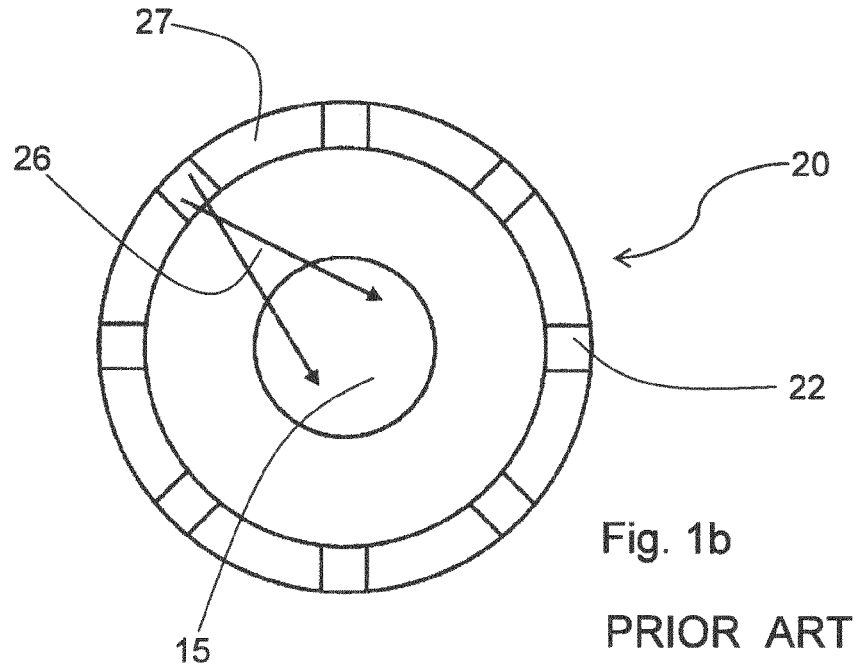
FIG. 1b shows a prior art ring light illuminator with annularly arranged light sources.

FIG. 1b shows another setup for a prior art ring illuminator 20. In an annular carrier 27 plural light sources 22 are arranged in an annular fashion. The light sources 22 emit light towards an area 15 to be illuminated. The light sources are LEDs, which typically are provided with shaping optics (not shown) to concentrate the light emitted from the LEDs around a predefined direction. As indicated by the cone 26, despite the shaping optics the light from a single light, source exhibits a divergence that is too large for many precision applications.

Figure 2:
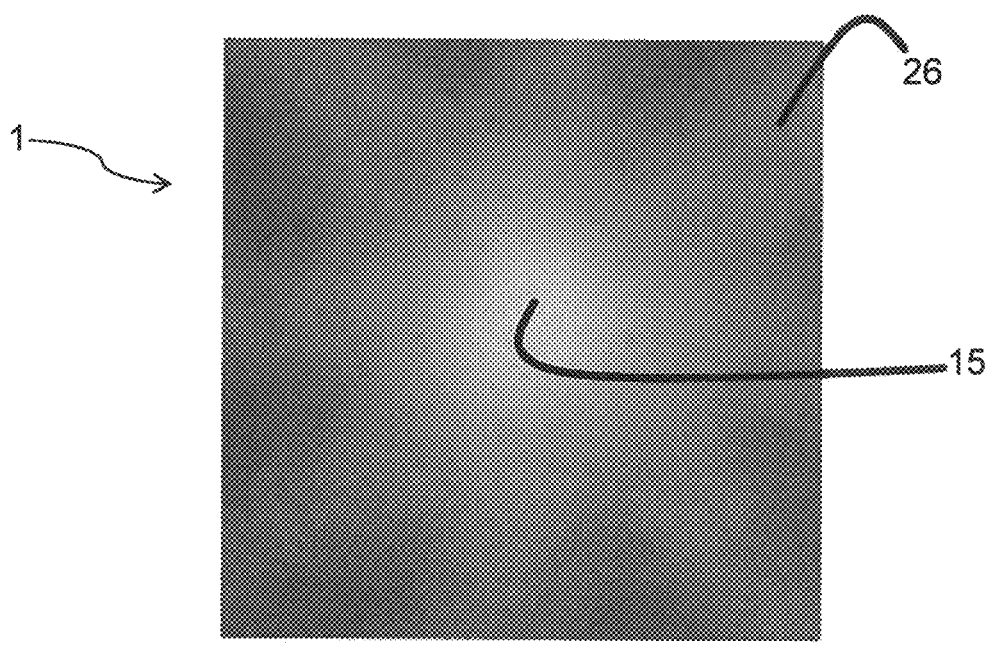
FIG. 2 shows the intensity distribution achievable with a prior art ring light illuminator as shown in FIG. 1b.

FIG. 2 shows the intensity distribution 1 achievable with a ring illuminator 20 as described in the context of FIG. 1b, comprising eight light sources with TIR lenses (see FIG. 3) as shaping optics. The illumination pattern is rather diffuse. The central region of the image shown is only moderately brighter than the regions illuminated by one of the cones 26, indicating that a considerable amount of intensity is directed towards off-centre regions of the area shown in the image rather than towards the central area 15 to be illuminated. The intensity distribution achievable with a ring illuminator 10 as described in the context of FIG. 1a is similar.

Figure 3:
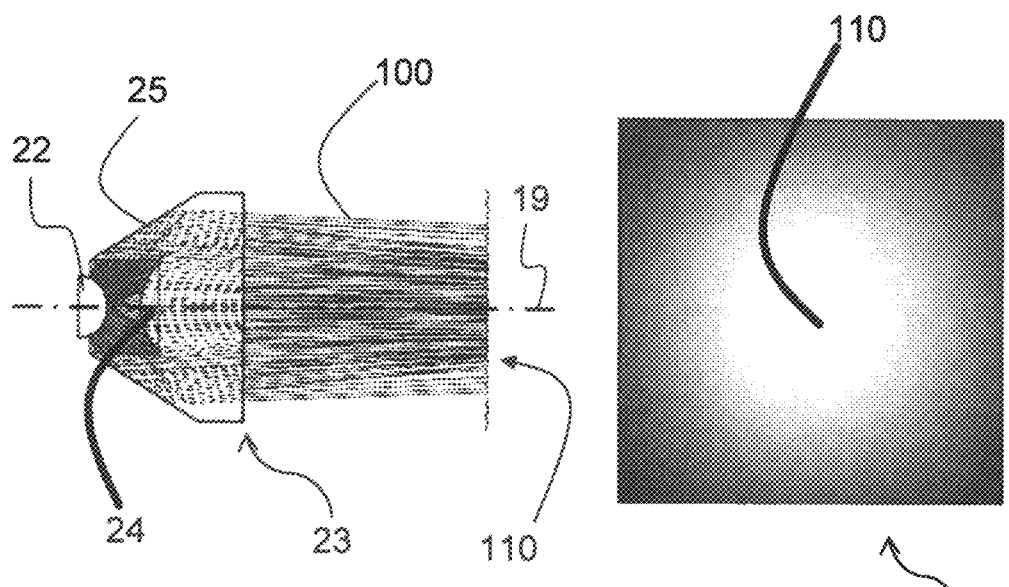
FIG. 3 shows a TIR lens and light rays as well as the intensity distribution created by it on a surface.

FIG. 3 shows a TIR (total internal reflection) lens 23. Light, indicated by light rays 100, from a light source 22, which here is an LED, is captured by the TIR lens 23 and directed towards a spot 110. Directing the light is achieved by two principles: A refractive lens portion 24 occupying a central part of the TIR lens 23 directs light rays 100 towards the spot 110 by refraction. Light rays 100 not hitting the refractive lens portion 24, but captured by the TIR lens 23, are directed towards the spot 110 by total internal reflection from a side surface 25 of the TIR lens 23. Also shown in FIG. 3 is the intensity distribution 2 of the spot 110 on a surface perpendicular to an optical axis 19 of the TIR lens 23. The intensity distribution 2 created by the TIR lens 23 is roughly Gaussian, so that there is maximum intensity in the centre of the spot 110, but there are also wide regions around the centre in which the intensity tails off, i.e. there are no clearly defined edges of the spot 110. A TIR lens 23 as described here can be used as shaping optics for a prior art ring illuminator 20 as described in the context of FIG. 1b. The intensity distribution 2 of the spot 110 without clearly defined edges is one reason why the intensity distribution 1 created by a cooperation of eight such combinations of light source 22 and TIR lens 23 is rather diffuse, as is evident from FIG. 2.

Figure 4:
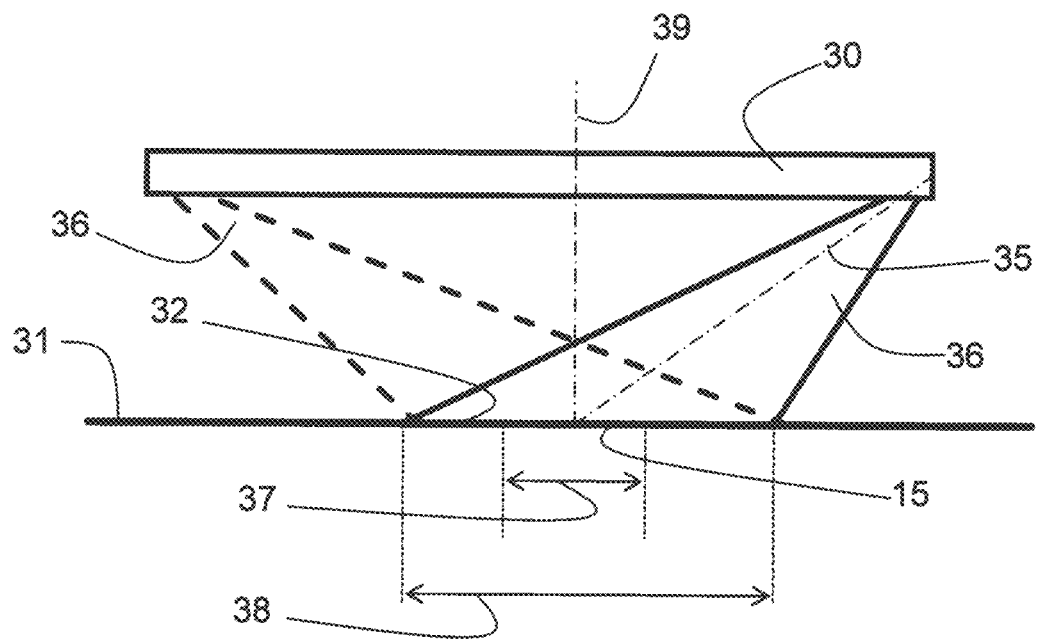
FIG. 4 is a schematic view of a ring light illuminator arranged above a surface to be illuminated.

FIG. 4 shows a typical arrangement of a ring light illuminator 30 above a surface 31 to be illuminated. The ring light illuminator 30 emits a plurality of light cones 36. In the drawing, two light cones 36 are shown; for the sake of better distinction, one of the light cones 36 has been drawn with solid lines, and one of the light cones 36 has been drawn with dashed lines. A light cone 36 intersects the surface 31 in a cross-sectional area 32 exhibiting a diameter 38. The diameter 38 is contained in a plane defined by a normal 39 of the surface 31 and an optical axis 35 of the light cone 36. The area 15 to be illuminated exhibits a diameter 37 typically smaller than the diameter 38 of the cross-sectional area 32. The area 15 to be illuminated typically is contained in the cross-sectional area 32.

Figure 5:
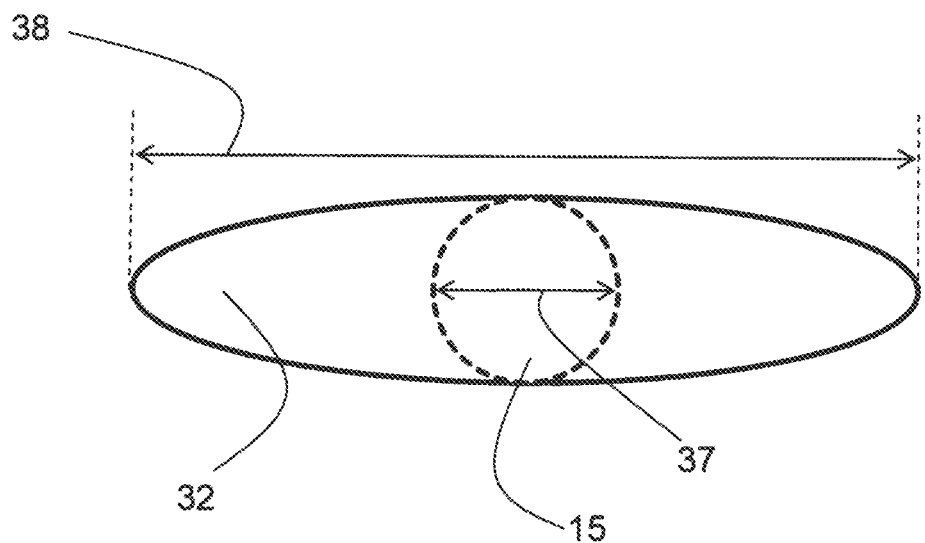
FIG. 5 illustrates the distortion of the beam cross section on a surface due to an oblique angle of illumination.

FIG. 5 shows a top view of the cross-sectional area 32 of FIG. 4. Also shown is the area 15 to be illuminated. The area 15 to be illuminated has a diameter 37 which is smaller than the diameter 38 of the cross-sectional area. The area 15 to be illuminated is contained in the cross-sectional area 32. The cross-sectional area 32 is elongated along the diameter 38 compared to the area 15 to be illuminated, due to the oblique angle of incidence of the light cone 36 (see FIG. 4) on the surface 31 (see FIG. 4). Therefore the light flux of the light cone 36 is distributed over the cross-sectional area 32, which is larger than the area 15 to be illuminated. The light intensity in the area 15 to be illuminated thus is reduced in comparison to the case of illumination of the area 15 to be illuminated along the normal 39 of the surface. In general this reduction of intensity is undesirable.

FIG. 6a illustrates the general geometrical situation for illuminating a surface 31 with a light cone 36 under an oblique angle 33. The angle 33 of illumination is defined here as the angle enclosed by a normal 39 of the surface 31 and an optical axis 35 of the light cone 36. The angle 33 here is different front zero, so that the illumination of the surface 31 does not occur along the normal 39 of the surface 31. The light cone 36 intersects the surface 31 in a cross-sectional area 32. Also shown is a cross section 34 of the light cone 36 perpendicular to the optical axis 35 of the light cone 36. A top view of the cross section 34 is shown in FIG. 6b, and a top view of the cross-sectional area 32 is shown in FIG. 6c. In the case shown the cross section 34 is circular and has a diameter D. The cross-sectional area 32 exhibits a first diameter 38 and a second diameter Q, perpendicular to the first diameter 38. The cross section 34 perpendicular to the optical axis 35 is taken here at the point where the optical axis 35 intersects the surface 31. Therefore in this case the diameter Q is equal to the diameter D. On the other hand the diameter 38, which is in the plane defined by the optical axis 35 and the surface normal 39 is elongated with respect to the diameter D of the cross section 34. The relative size of the diameters 38 and D is determined by the angle 33 and the divergence of the light cone 36 in the example shown. If is obvious to a person skilled in the art that the elongation of a diameter 38 of the cross-sectional area 32 with respect to the diameter D of the cross section 34 not only occurs for light cones, i.e. divergent light beams, but also for convergent light beams and light beams of parallel light rays. The elongation evidently also occurs if the cross section 34 of the light beam perpendicular to the optical axis 35 of the light beam has a shape different from circular, for example elliptical, rectangular, square, polygonal, or any other.

Figure 7:
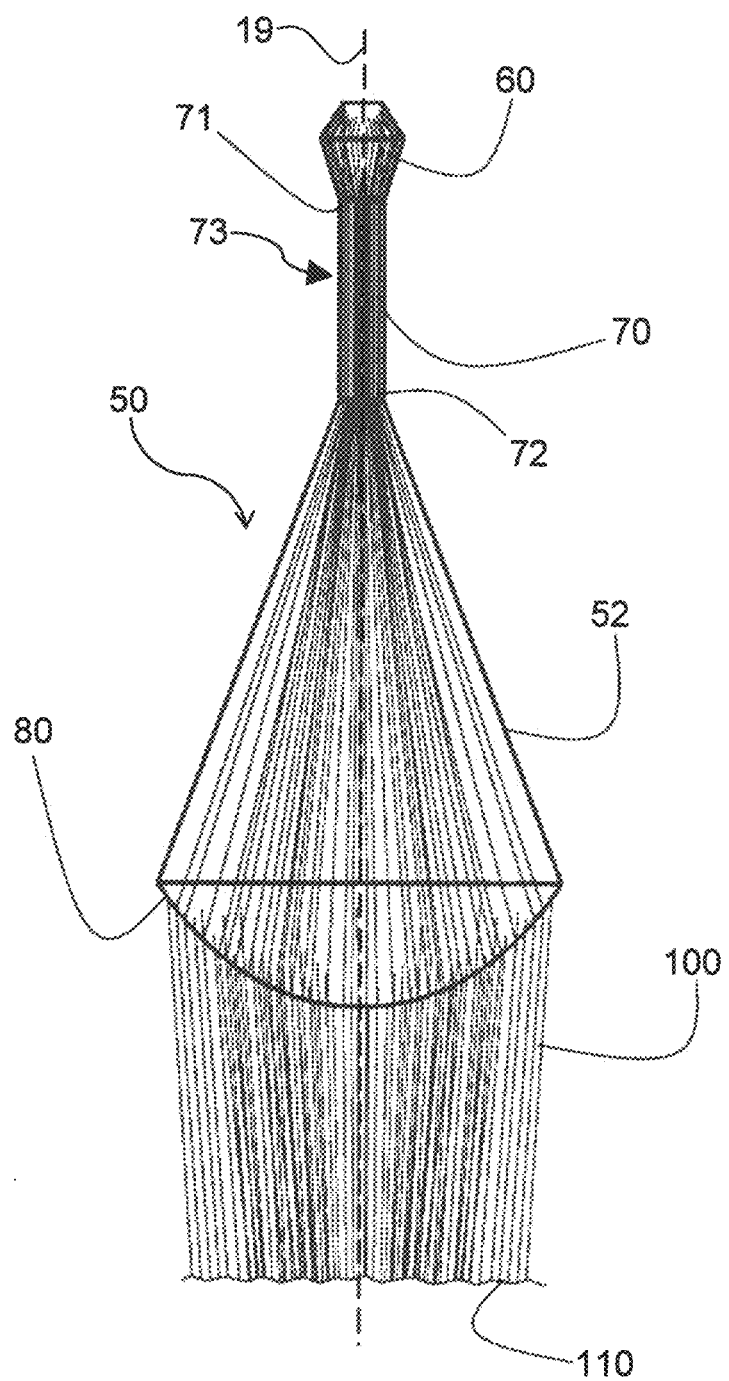
FIG. 7 shows a beam shaper according to the invention and light rays.

FIG. 7 shows a beam shaper 50 according to a preferred embodiment, comprising a light collector portion 60, a homogenizing portion shaped as a rod 70, a cone section 52, and an anamorphic portion 80, which here is a cylinder lens performing both an anamorphic beam shaping function and a light focusing function. A light source (not shown) is inserted in the light collector portion 60 and emits light indicated by the light rays 100. The light collector portion 60 collects light from the light source and directs it into the homogenizing rod 70, through a first end 71 of the homogenizing rod 70. The homogenizing rod 70 is aligned along an optical axis 19 of the beam shaper 50. The optical axis 19 of the beam shaper coincides with an optical axis of the light collector portion 60. In the homogenizing rod 70 the light is homogenized by reflection, typically multiple reflection, from the side surfaces 73 of the homogenizing rod 70. The beam shaper 50 is manufactured as one piece, for example by injection molding, from a material that is transparent for the wavelengths of light the beam shaper is intended to be used with, like for example a plastic material or glass, and the reflection from the side surfaces 73 is total internal reflection. The light exits the homogenizing rod 70 through a second end 72 of the homogenizing rod 70, and enters the cone section 52. From there it reaches the anamorphic portion 80, which directs the light onto a spot 110. The intensity distribution of the spot 110 is an image of the second end 72 of the homogenizing rod 70, with additional anamorphic deformations due to the anamorphic beam shaping function of the anamorphic portion 80. The spot 110 shown in the drawing is in a surface perpendicular to the optical axis 19 of the beam shaper 50. The purpose of the cone section 52 is to establish a fixed distance between the second end 72 of the homogenizing rod 70 and the anamorphic portion 80. As the beam shaper 50 is manufactured as one piece, no alignment of individual components, i.e. of light collector portion 60, homogenizing rod 70, and anamorphic portion 80, is necessary during assembly of an optical system. This simplifies handling of the beam shaper 50, and the assembly of optical systems, like for instance a ring light illuminator 20, of the type shown in FIG. 1b; contrary to prior art, however, beam shapers 50 just discussed, rather than TIR lenses, are used as shaping optics in embodiments of ring light illuminators according to the invention. The beam shaper 50 can of course also be used for other illumination tasks and is not limited to ring light, illumination.

Figure 8A:
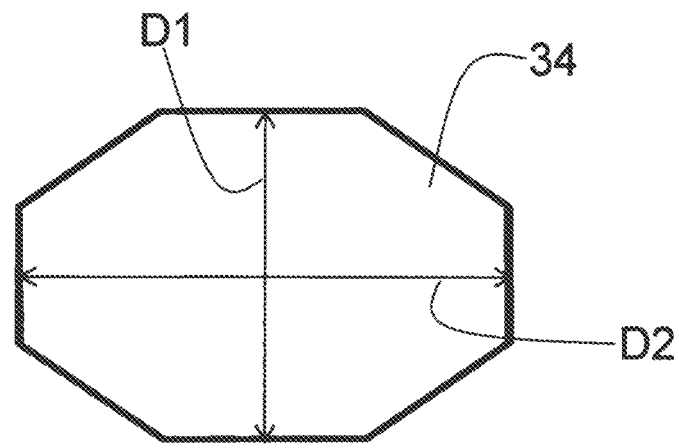
FIG. 8a schematically shows a cross section of a beam of light created by the beam shaper of FIG. 7, where the cross section is perpendicular to an optical axis of the beam shaper.

FIG. 8a schematically shows a cross section 34 of a beam of light created by the beam shaper 50 of FIG. 7, where the cross section 34 is perpendicular to the optical axis 19 (see FIG. 7) of the beam shaper 50. This cross section 34 would correspond to the shape of a spot 110 (see FIG. 7) created on a surface 31 (see FIG. 6a) in the case of illumination along a surface normal 39 (see FIG. 6a), i.e. in the case that the optical axis 19 of the beam shaper 50 is parallel to the surface normal 39. The cross section 34 here is octagonal, because in the embodiment of the beam shaper 50 shown in FIG. 7 the homogenizing rod 70 has a cross section shaped as a regular octagon. The shape of the cross section 34 of the beam of light is octagonal, but not shaped as a regular octagon. A first diameter D1 of the cross section is smaller than a second diameter D2 along a direction perpendicular to the direction of the first diameter D1. This deformation of the beam cross section 34 is caused by the anamorphic beam shaping due to the anamorphic portion 80 (see FIG. 7).

Figure 8B:
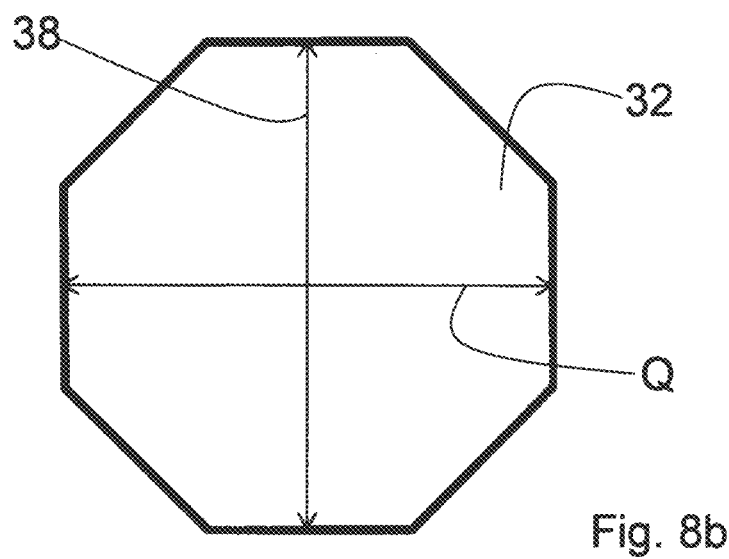
FIG. 8b schematically shows a cross-sectional area of a beam of light as described in the context of FIG. 8a on a surface onto which the beam of light impinges under an oblique angle.

FIG. 8b schematically shows a cross-sectional area 32 of a beam of light as described in the context of FIG. 8a on a surface 31 onto which the beam of light impinges under an oblique angle 33, as described in FIG. 6, there for the case of a light cone 36. A direction of a diameter 38 is along an intersection between the surface 31 and a plane comprising the optical axis of the light beam and a surface normal 39. In the case of FIGS. 8a and 8b the arrangement is such that the direction of the first diameter D1 of the cross section 34 also is within this plane. The anamorphic portion 80 is configured such that the reduction of the first diameter D1 of the cross section 34 of the beam due to the anamorphic beam shaping compensates the elongation of the cross-sectional area 32 along the direction of the diameter 38 caused by the oblique angle 33 of incidence of the light beam on the surface 31. In the case shown, a diameter Q of the cross-sectional area 32 perpendicular to the diameter 38 is unaffected by both the anamorphic beam shaping and the oblique angle of incidence. For the configuration shown, the diameter Q of the cross-sectional area 32 is equal to the second diameter D2 of the cross section 34 of the light beam.

Figure 9:
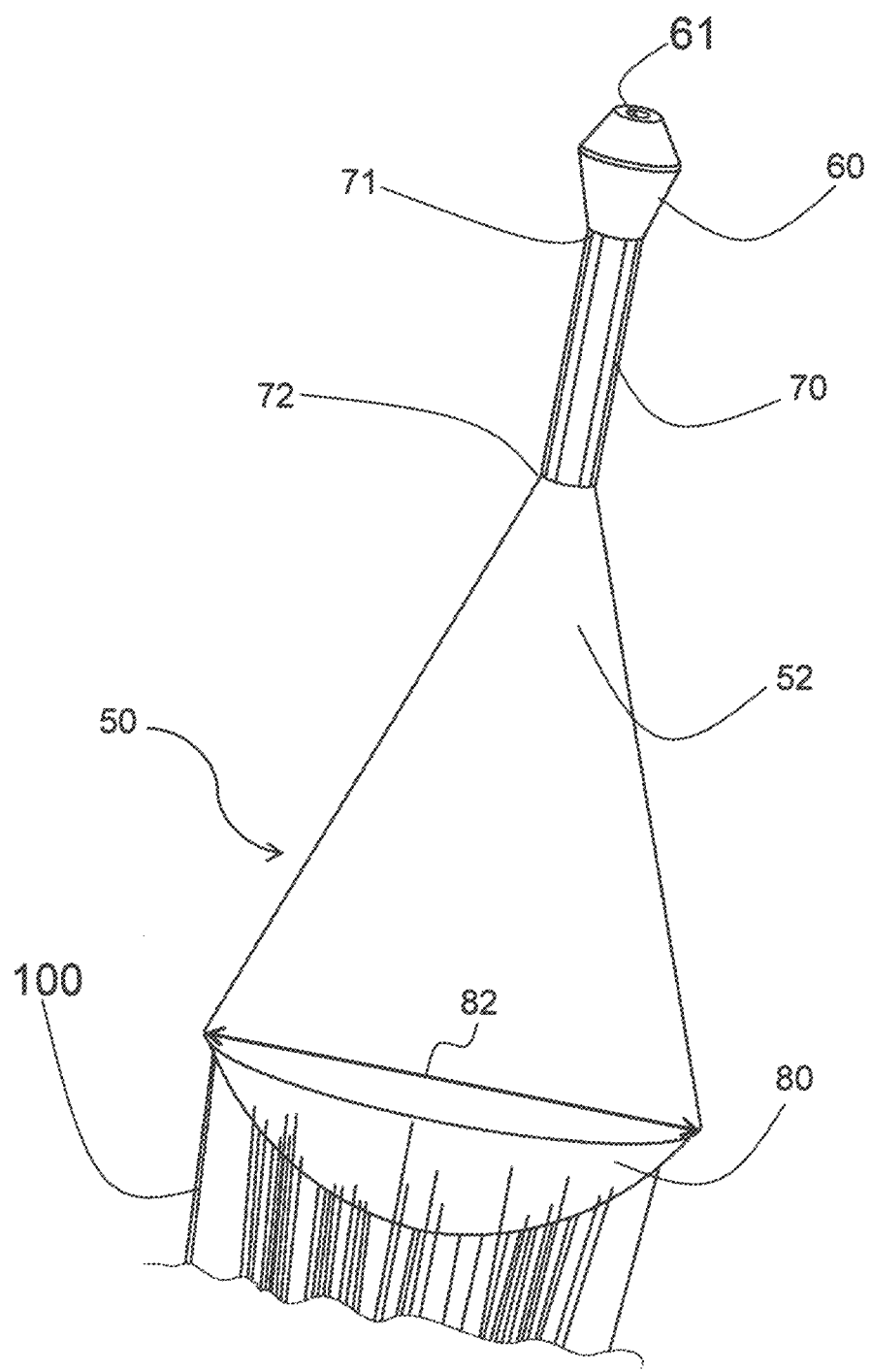
FIG. 9 is a perspective view of a beam shaper according to the invention.

FIG. 9 shows a perspective view of a beam shaper 50 according to the invention, as has already been shown in FIG. 7. Here light rays 100 exiting the anamorphic portion 80 are shown. The configuration of such a beam shaper 50 has already been discussed in the context of FIG. 7. The light collector portion 60 exhibits a cavity 61 into which a light source (not shown) is to be introduced. The general configuration of the light collector portion 60 corresponds to that of a TIR lens 23, as shown in FIG. 3. The diameter 82 of the anamorphic portion 80 regulates the number of beam shapers 50 that can be arranged in a ring-illuminator 20.

Figure 10A:
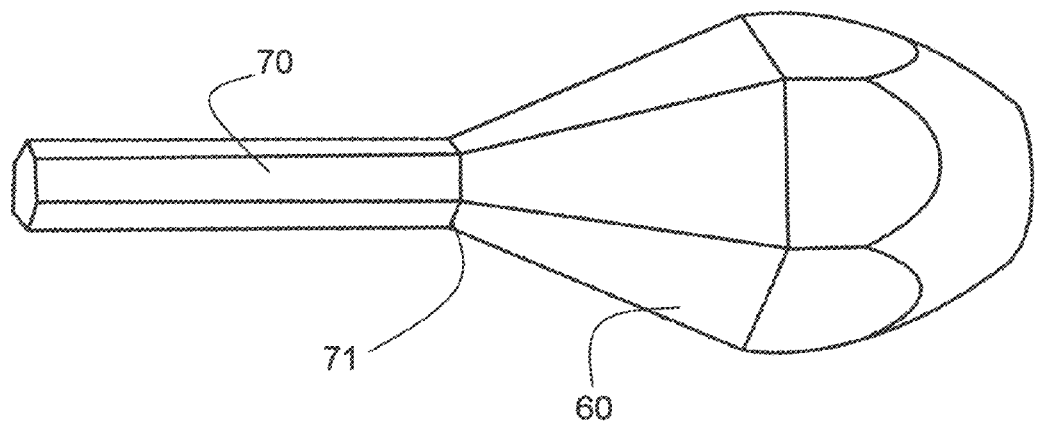
FIG. 10a is a perspective view of a light collector and a homogenizing rod.
Figure 10B:
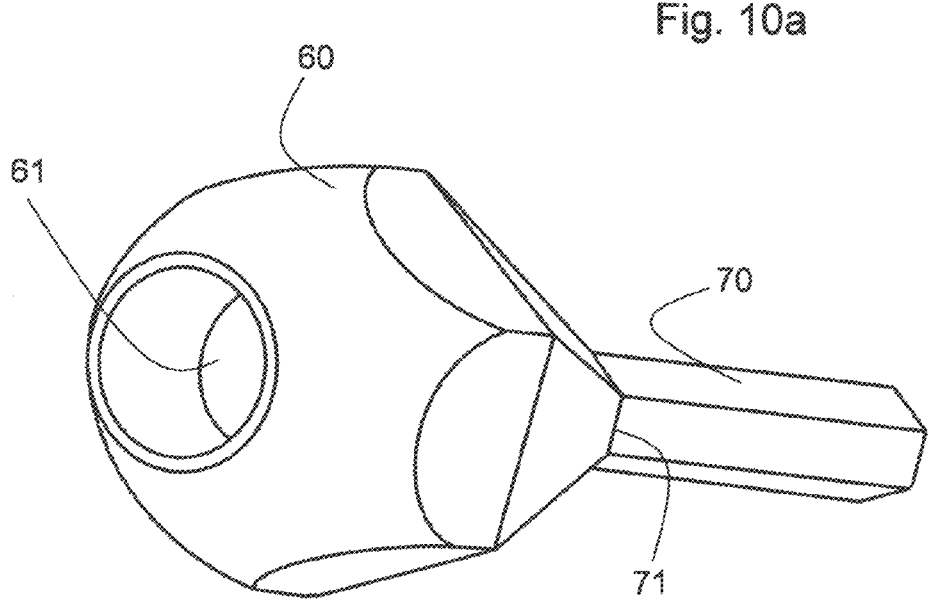

FIGS. 10a and 10b are perspective views of a light collector 60, or light collector portion 60, respectively, as used for a beam shaper 50 according to the invention, as shown in FIGS. 7 and 9, as well as in shaping optics for a ring light illuminator according to the invention, which may be composed of several pieces. Only a part of the homogenizing rod 70 attached to the light collector 60 is shown. The rod 70 here has a hexagonal cross section, and the shape of the light collector 60 is adapted to the cross section of the rod 70, also exhibiting a hexagonal cross section in a section adjacent to the first end 71 of the rod 70. FIG. 10b clearly shows the cavity 61 of the light collector 60, into which a light source (not shown), typically an LED, is to be inserted.

Figure 11:
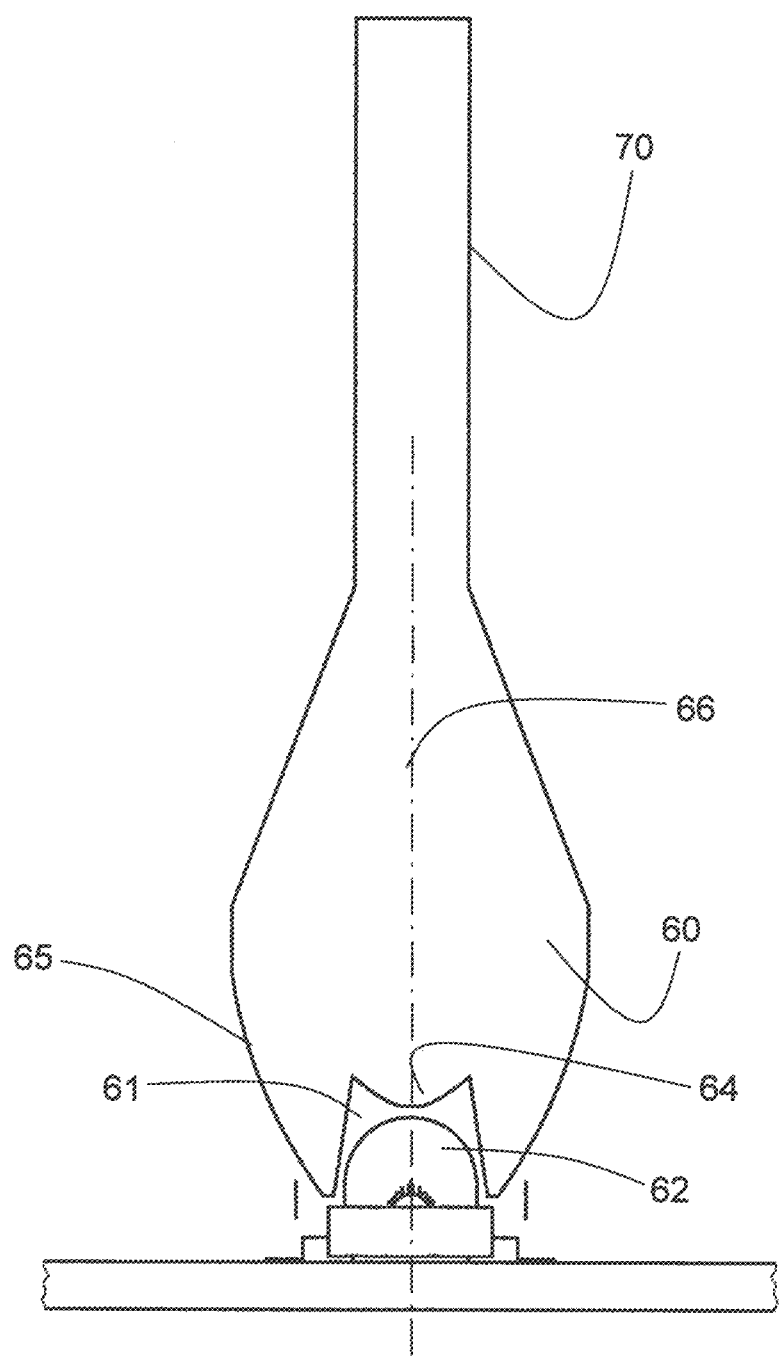
FIG. 11 shows a light source introduced into a cavity in a light collector with a homogenizing rod.

FIG. 11 shows a sectional view of a light collector 60 and part of a homogenizing rod 70. A LED 62 is introduced in the cavity 61 of the light collector 60. Analogous to the TIR lens 23 of FIG. 3, the light collector 60 exhibits a refractive lens portion 64, which collects light emitted into a central region around an optical axis 66 of the light collector 60. The cross section of this region is determined by the shape and size of the refractive lens portion 64. Light emitted by the LED into a region outside the central region is directed into the homogenizing rod 70 by total internal reflection from a side surface 65 of the light collector 60.

Figure 12:
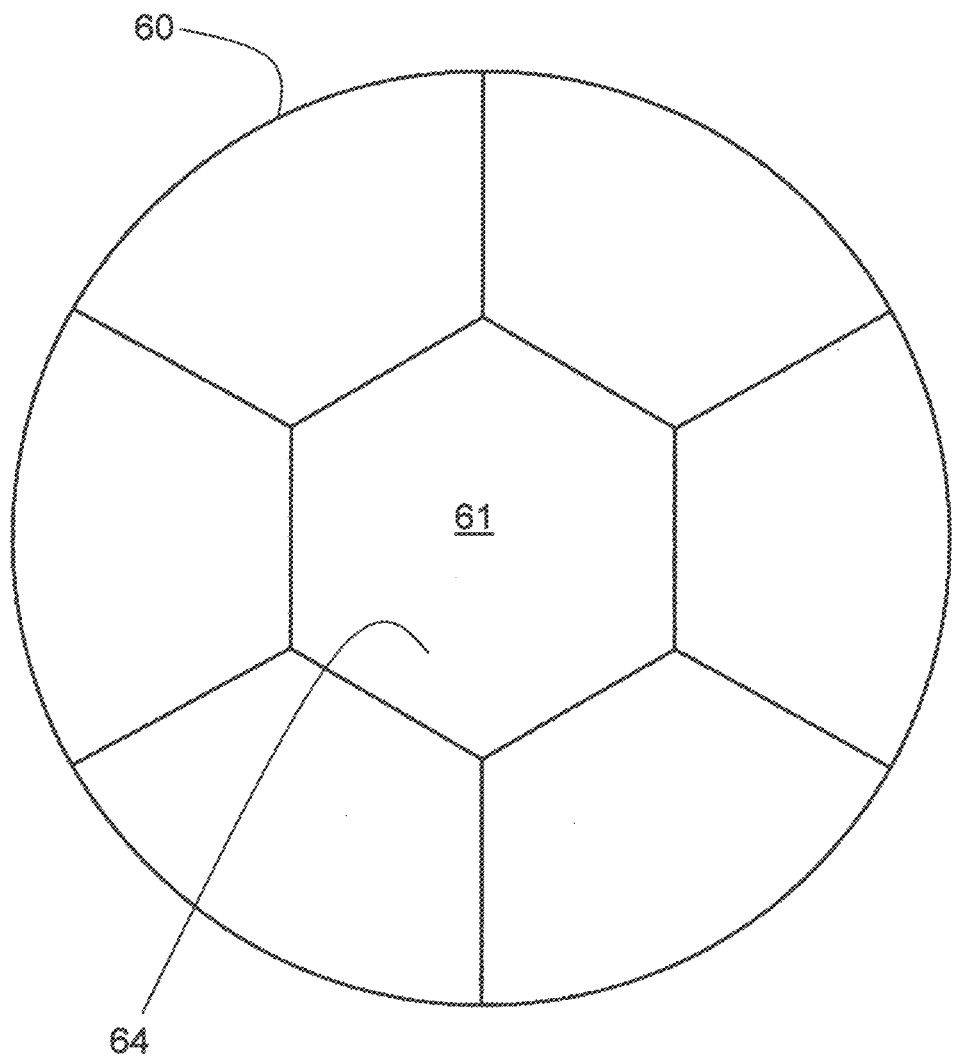
FIG. 12 is a top view of the cavity in a light collector.

FIG. 12 is a top view of the cavity 61 in a light collector 60, into which a light source like the LED 62 in FIG. 11 is to be inserted. The cavity 61 and the refractive lens portion 64 here have a hexagonal cross section.

Figure 13:
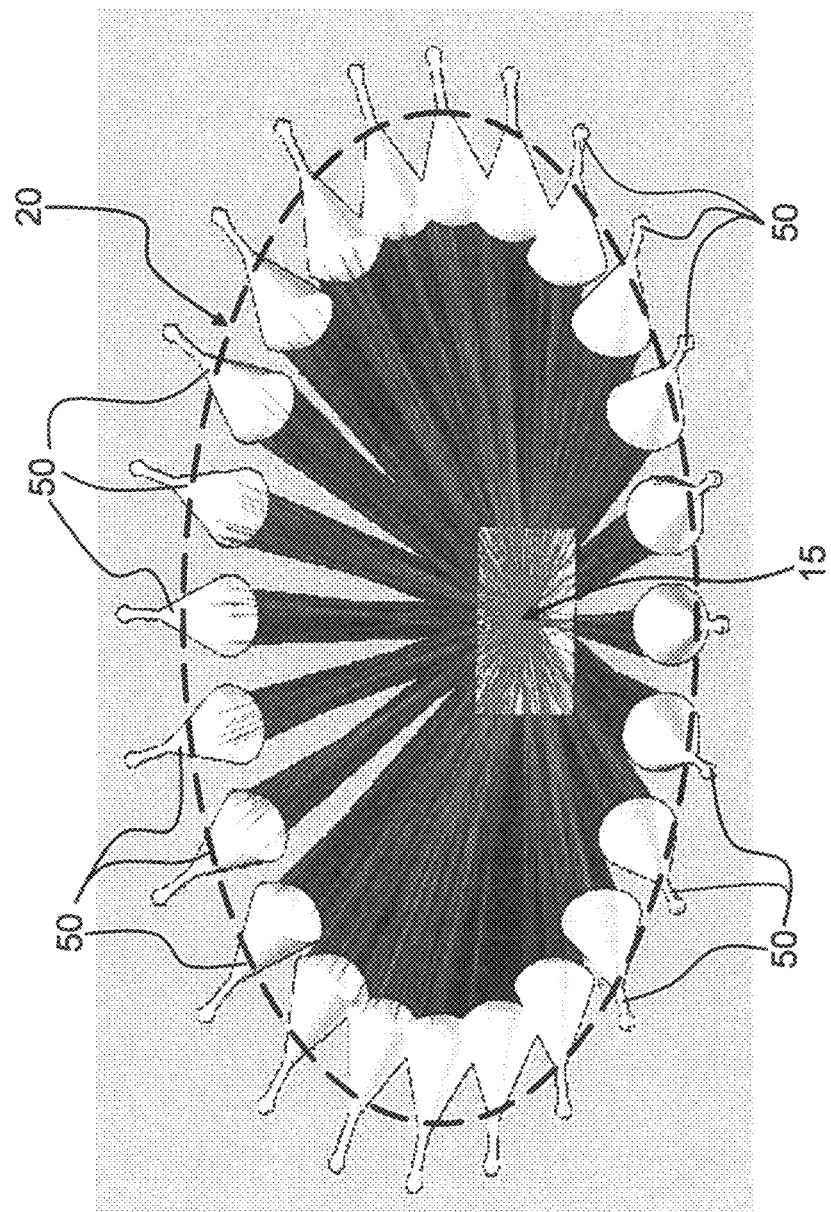
FIG. 13 is an embodiment of a possible implementation of a plurality of beam shapers arranged in ring to constitute the ring-illuminator according to the invention.

FIG. 13 is an embodiment of a possible implementation of a plurality of beam shapers 50 arranged in ring to form the ring-illuminator 20 according to the invention. The plurality of beam shapers 50 arranged in the ring-illuminator 20 provides a homogeneous illumination for the area 15 to be illuminated. The diameter 82 of the anamorphic portion 80 (see FIG. 9) regulates the number of beam shapers 50 arranged in the ring-illuminator 20. In the embodiment shown here, the diameter 82 of the anamorphic portion 80 is 30 mm, which results in approximately 24 beam shapers 50 arranged in the ring-illuminator 20.

Figure 14:
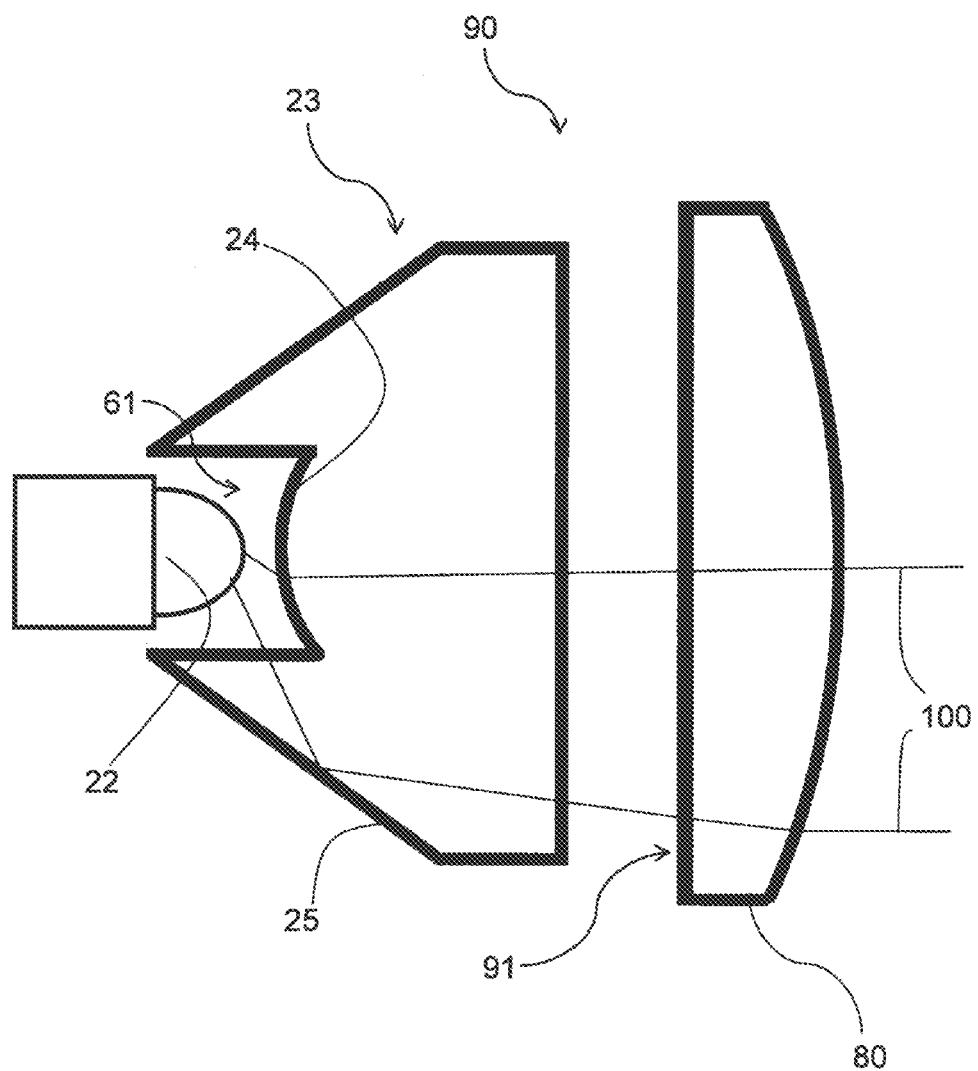
FIG. 14 is a schematic view of an embodiment of another beam shaper according to the invention.

FIG. 14 shows an embodiment of another beam shaper 90 according to the invention. A TIR lens 23 as described in the context of FIG. 3 functions as a light collector. In this embodiment the TIR lens 23 is configured to collect light from a light source 22 inserted into a cavity 61 of the light collector or TIR lens 23, and thus encompassed by the light collector, and directs the light towards an anamorphic system 80. The anamorphic system 80 performs an anamorphic beam shaping function and in specific embodiments in addition may perform a light focusing function. In the embodiment shown, the anamorphic system 80 is a cylinder lens. A beam shaper 90 as shown may be used in a ring light illuminator according to the invention, but is not limited to this specific use. In any case the anamorphic beam shaping performed by the anamorphic system 80 may advantageously be employed to compensate the elongation of a cross-sectional area of the light beam from the beam shaper 90 with a surface, as discussed in the context of FIGS. 4, 5, 6a, 6b, and 6c, if the beam from the beam shaper 90 is directed onto the surface under an oblique angle. An additional homogenization of the light beam may be achieved by providing a texture on at least one of the optical surfaces of the beam shaper 90, i.e. on at least one of the surfaces passed by the light rays 100 from the light source 22. One possible surface on which a texture for homogenization of the light beam may be provided is surface 91. In the drawing, for the sake of clarity, only two light rays 100 from the light source 22 are shown, one light ray passing a refractive lens portion 24 of the TIR lens 23, and thus directed to the anamorphic element 80 by refraction, and another light ray 100, impinging on a side surface 25 of the TIR lens 23, and directed to the anamorphic element 80 by total internal reflection from the side surface 25. Since the beam shaper 90 of this embodiment does not exhibit a homogenizing rod 70 as the beam shaper 50 of FIG. 7, it is of a more compact design than the latter.

The invention has been described with reference to specific embodiments. It is obvious to a person skilled in the art, however, that alterations and modifications can be made without leaving the scope and the spirit of the subsequent, claims.

REFERENCE NUMERALS 1, 6 intensity distribution
2, 3, 4, 5 intensity distribution
10, 20, 30 ring light illuminator
11 optical fibre
12 arc lamp
13 optical element
14 end of optical fibre
15 area to be illuminated
16, 26 cone of light
17, 27 carrier
19, 66 optical axis
22 light source
23 TIR lens
24, 64 refractive lens portion
25, 65 side surface
31 surface
32 cross-sectional area
33 angle
34 cross section
35 optical axis of light cone
36 light cone
37 diameter of area to be illuminated
38 diameter of cross-sectional area
39 surface normal
50 beam shaper
52 cone section
60 light collector, light collector portion
61 cavity 62 LED
70 homogenizing rod, homogenizing portion shaped as a rod
71 first end of homogenizing rod
72 second end of homogenizing rod
73 side surface of homogenizing rod
80 anamorphic system, anamorphic portion
82 diameter of anamorphic system/anamorphic portion
90 beam shaper
91 surface for texture
100 light ray
110 spot
D diameter of cross section
D1 first diameter of cross section
D2 second diameter of cross section
Q diameter of cross sectional area

What is claimed is:

1. Ring light illuminator for illuminating an area on a surface, comprising:
 a plurality of annularly arranged light sources;
 a light collector assigned to each light source and encompassing a light emitting surface of the respective light source; and
 an anamorphic system arranged in an optical axis of each light collector, configured to direct light into the area to be illuminated.

2. Ring light illuminator according to claim 1, wherein the anamorphic system in addition performs a light focusing function.

3. Ring light illuminator according to claim 2, wherein at least one anamorphic system is a toroidal lens or a cylinder lens.

4. Ring light illuminator according to claim 1, wherein the anamorphic system has a first optical element with a light focusing function and a second optical element performing anamorphic beam shaping.

5. Ring light illuminator according to claim 4, wherein the second optical element is a toroidal lens or a cylinder lens.

6. Ring light illuminator according to claim 1, wherein to each light collector there corresponds a homogenizing means for homogenizing light from the light collector.

7. Ring light illuminator according to claim 6, wherein the homogenizing means is a rod.

8. Ring light illuminator according to claim 7, wherein the homogenizing function of the rod is based on total internal reflection of light within the rod.

9. Ring light illuminator according to claim 7, wherein a light collector and a corresponding rod form a one-piece unit.

10. Ring light illuminator according to claim 7, wherein a light collector, a corresponding rod, and a corresponding anamorphic system form a one-piece unit.

11. Ring light illuminator according to claim 6, wherein the homogenizing means is a texture provided on the light collector.

12. Ring light illuminator of claim 1, wherein each light source exhibits at least one light emitting diode (LED).

13. Ring light illuminator of claim 1, wherein the ring light illuminator exhibits plural cooling fins.

14. Ring light illuminator for illuminating an area on a surface, comprising:
 a plurality of annularly arranged light sources; and
 a beam shaper assigned to each light source, wherein the beam shaper is injection-molded as one piece from a plastic material, each beam shaper exhibiting
  a light collector portion encompassing a light emitting surface of one light source, wherein the function of the light collector portion is based on total internal reflection and on refraction;
  a light homogenizing portion shaped as a rod, arranged and configured to receive light from the light collector portion, wherein the light homogenizing function of the rod is based on total internal reflection of the light within the rod; and
  an anamorphic portion, performing a lensing function and an anamorphic beam shaping function.

15. Beam shaper, comprising;
 a light collector configured to encompass a light emitting surface of a light source;
 a homogenizing rod configured to homogenize light received from the light collector; and
 an anamorphic system for imaging an end of the homogenizing rod opposite the light collector into an area to be illuminated.

16. Beam shaper according to claim 15, wherein the beam shaper is molded from a plastic material.

17. Beam shaper according to claim 15, wherein the beam shaper is made of glass.

18. Beam shaper according to claim 15, wherein the anamorphic system performs a light focusing function.

19. Beam shaper according to claim 18, wherein the anamorphic system is a toroidal lens or a cylinder lens.

20. Beam shaper according to claim 15, wherein the anamorphic system has a first optical element with a light focusing function and a second optical element performing the anamorphic beam shaping.

21. Beam shaper according to claim 20, wherein the second optical element is a toroidal lens or a cylinder lens.

22. Beam shaper according to claim 15, wherein the beam shaper is manufactured as one piece.

23. Beam shaper injection-molded as one piece from a plastic material, the beam shaper comprising
 a light collector portion configured to encompass a light emitting surface of a light source, wherein the function of the light collector portion is based on total internal reflection and on refraction;
 a light homogenizing portion shaped as a rod, arranged and configured to receive light from the light collector portion, wherein the light homogenizing function of the rod is based on total internal reflection of the light within the rod; and
 an anamorphic portion, configured to image an end of the homogenizing portion opposite the light collector portion into the area to be illuminated, therein performing a lensing function and an anamorphic beam shaping function.

24. Beam shaper, comprising:
 a light collector configured to encompass a light emitting surface of a light source; and
 an anamorphic system arranged on an optical axis of the light collector configured to receive light from the light collector and to direct it onto an area to be illuminated.

25. Beam shaper of claim 24, wherein the beam shaper is manufactured as one piece.

26. Beam shaper according to claim 24, wherein the anamorphic system exhibits a light focusing function.

27. Beam shaper according to claim 24; wherein the light collector performs its light collecting function by a combination of total internal reflection and refraction.

28. Beam shaper injection-molded as one piece from a plastic material, the beam shaper comprising:
 a light collector portion configured to encompass a light emitting surface of one light source, wherein the function of the light collector portion is based on total internal reflection and on refraction; and an anamorphic portion, arranged on an optical axis of the light collector portion, and directing light from the light collector portion into the area to be illuminated, therein performing a lensing function and an anamorphic beam shaping function.

29. Method for homogeneously illuminating an area on a surface with a plurality of light sources, comprising the following steps:

arranging the plurality of light sources in an annular fashion about the area to be illuminated and at a distance from the surface;

collecting light emitted by each light source with a beam shaper into a respective beam of a predefined cross section, wherein an optical axis of the beam shaper is directed towards the surface under an oblique angle with the surface;

anamorphically deforming the cross-section of each beam and directing the beam into the area to be illuminated under the oblique angle, wherein the anamorphic deformation of the cross section of the beam is such that a deformation of a cross-sectional area of the beam on the surface due to the oblique angle of incidence is compensated.

* * * * *